(12) United States Patent
Hajjar et al.

(10) Patent No.: US 6,190,171 B1
(45) Date of Patent: Feb. 20, 2001

(54) METHOD AND APPARATUS FOR TOOTH RESTORATION

(76) Inventors: Victor J. Hajjar, 1300 Galen Rd., Harrisburg, PA (US) 17112; John Robert Studer, 135 Grandview Rd., Hummelstown, PA (US) 17036

( * ) Notice: Under 35 U.S.C. 154(b), the term of this patent shall be extended for 0 days.

(21) Appl. No.: 09/357,886

(22) Filed: Jul. 21, 1999

Related U.S. Application Data

(63) Continuation of application No. PCT/US98/00910, filed on Jan. 23, 1998, which is a continuation-in-part of application No. 08/785,316, filed on Jan. 23, 1997, now Pat. No. 5,813,859.

(51) Int. Cl.[7] ................................................ A61C 5/08
(52) U.S. Cl. ........................ 433/218; 433/223; 433/76; 433/53
(58) Field of Search ............................. 433/218, 219, 433/223, 76, 53

(56) References Cited

U.S. PATENT DOCUMENTS 5,135,393 * 8/1992 Eidenbenz et al. ..................... 433/53
5,383,752 * 1/1995 Rheinberger et al. ........... 433/223 X

* cited by examiner

*Primary Examiner*—Nicholas D. Lucchesi
(74) *Attorney, Agent, or Firm*—Burns, Doane, Swecker & Mathis, LLP

(57) ABSTRACT

The present invention is directed to enhancing the accuracy with which tooth restorations are performed, including the manner by which a tooth is prepared and fit with a dental prosthetic. Further, the present invention is directed to reducing the skill dependent tasks associated with tooth restoration, while at the same time, improving the precision with which these procedures are performed. By improving the accuracy of restoration procedures, any need to repeat these procedures for a given patient can be eliminated and patient comfort can be improved.

12 Claims, 6 Drawing Sheets

METHOD AND APPARATUS FOR TOOTH RESTORATION

This application is a continuation of PCT/US98/00910 filed Jan. 23, 1998, which is a C-I-P of Ser. No. 08/785,316 filed Jan. 23, 1997, U.S. Pat. No. 5,813,859.

BACKGROUND OF THE INVENTION

1. Field of the Invention

The present invention relates generally to the restoration of teeth, and more particularly, to methods and devices for improving the accuracy and simplifying the process of performing such restorations.

2. State of the Art

Presently, numerous methods exist for the restoration of teeth by dentists, including the use of artificial tooth material (such as gold or porcelain) to form a cast-restoration or a metal-ceramic restoration (i.e., dental prosthetics such as crowns). Prosthetic crowns are typically used to repair decayed tooth structure where support from the original tooth structure is either marginal, or unavailable.

Known techniques for preparing a tooth to receive a crown are susceptible to numerous variables, some of which are within the dentist's control and some of which are not. All of these variables can detrimentally influence the accuracy with which: (1) the tooth is prepared to receive the crown; (2) the crown is prepared for placement on the tooth; and (3) the manner by which the crown is fit to and fixed on the prepared tooth.

For example, in preparing the original tooth to receive the crown, a dentist will typically use various shaped diamond burs in a high speed hand tool to remove approximately 2 mm of exterior tooth structure. The coronal portion of the tooth is shaped so that when a prosthetic crown is received from a laboratory, it will be of the approximate size and shape of the patient's original coronal portion prior to preparation. Because tooth preparation is performed totally by manipulation of a hand tool, and because the skill required for such tooth preparation will vary among dentists, the precision with which a tooth is prepared will vary widely.

Further, the quality of the prosthetic crown will vary based on the skill of the person who actually produces the crown (e.g., laboratory technician). More particularly, after the patient's tooth has been shaped to receive the prosthetic crown, an impression is formed from the prepared tooth by placing impression material into the patient's mouth (i.e., to form a negative impression of the prepared and adjacent teeth). To accurately prepare the impression, all gingival bleeding must be stopped and the margin of the gum tissue must be retracted from the lower portion of the tooth. The impression material must then be properly injected into the sulcus area of the tooth. A tray which contains a combination of impression materials is then applied with pressure over the teeth in the area of the prepared tooth, including the prepared tooth.

Despite efforts by the dentist to obtain an accurate impression of the prepared tooth, many factors can detrimentally influence quality of the impression. For example, the ability of the dentist to maintain a dry field of operation in the area of the prepared tooth can inhibit accuracy of the impression. The retraction of the gingival tissue can also affect the accuracy of the impression, as can the dentist's technique in obtaining the impression (i.e., the general care in obtaining an accurate impression).

Once the impression has been produced by the dentist, a laboratory technician will set die pins in the impression and then form a master impression as a die (e.g., plaster models) of the patient's teeth. The technician will set the occlusal bite registration and articulate the models of the patient's teeth. Afterwards, the laboratory technician will saw the die to remove the tooth of interest, then trim the die of the tooth and mark the marginal finish line. The sub-structure is then waxed for preparation of the prosthetic crown.

After a wax pattern has been formed, it is converted (i.e., cast or machined) into a sub-structure (e.g., coping) of the crown. It is a challenge to produce a coping that will comply with acceptable tolerances, given the variables associated with the quality of the impression, the skill of the technician and the proper selection of die materials.

U.S. Pat. No. 5,135,393, assigned to Mikrona, describes a coping mechanism for producing parts such as non-metal copings. As described therein, a three-dimensioned pattern is sensed (e.g., traced) with a feeler pin, and then sensed deflections or displacements of the feeler pin are transferred to a motor driven machining tool. As the pattern is traced, the motor driven machining tool operates upon a blank to fabricate a matching three-dimensional coping. The coping is later used by the dental laboratory to build-up a finished crown.

That is, once the machined coping has been produced, it is processed with a porcelain build-up. The build-up material incorporates specific shading and color effects to simulate the enamel of the original tooth. The porcelain build-up is then vacuum fired.

The combination of producing a coping, followed by building-up the coping with porcelain, are thus required to produce the prosthetic crown. The final stages of crown preparation include finishing the porcelain build-up, after which the anatomy of the original tooth structure is carved therein. The porcelain crown is then glazed. Where the crown is formed of cast metal, the cast exterior of the crown is sand-blasted to remove external oxidation. The metal interior is then polished and the fit, shading and prosthetics of the crown are quality checked. The finished crown is then returned to the dentist for placement onto the prepared tooth structure.

Processes which involve using devices such as those described in U.S. Pat. No. 5,135,393 are not practical for widespread use in dentistry for a variety of reasons. These devices involve complex and timely processes for producing a finished prosthetic suitable for placement in a patient's mouth.

For example, to produce a finished crown, the process described in the '393 patent requires: (1) initially making a dental impression of the patient's teeth; (2) producing a hand made pattern (i.e., template), such as a template of a three-dimensional dental coping from the impression; (3) using an apparatus as described in the '393 patent to produce a non-metal coping by tracing the template and concurrently machining an oversized blank; (4) building-up the machined, non-metal coping in a dental laboratory with a crown material, such as porcelain; (5) sintering the crown material on the non-metal coping and returning the finished crown to the dentist for final adjustment and placement in the patient's mouth.

Thus, while an apparatus as described in the '393 patent is useful in machining dental parts, it does little to reduce the time and complexity associated with producing finished dental prosthetics such as crowns and bridges. The process of shipping an impression from the dentist's office to the laboratory technician, the preparation of the crown and the returning of the crown to the dentist typically involves a period of approximately two weeks. Upon receipt of the prosthetic crown from the laboratory, the dentist removes a temporary crown which had been placed over the prepared tooth of the patient following preparation of the impression. The permanent crown is then cemented into place. The dentist's skill is again called upon to ensure proper fit, occlusion bite registration and aesthetics of the prosthetic crown. While the dentist can modify the occlusion of the crown, inaccuracies in fit can require that a new crown be prepared and the entire process described above repeated, thus leading to increased time delays and patient discomfort due to prolonged use of a temporary crown. In some cases, if the crown does not accurately fit, the dentist will use a bur to ground the interior; however, the use of a bur to shape the crown interior alters the fit and therefore detrimentally affects the marginal seal.

Thus, it would be desirable to improve the accuracy with which tooth restorations are performed. Further, it would be desirable to reduce the skill-dependent tasks associated with tooth restoration, and to reduce the cost associated with such procedures, without compromising the quality of these procedures. Ideally, it would be desirable to provide a process which would enable a crown to be completely produced in a dental office, within the course of a day.

SUMMARY OF THE INVENTION

Accordingly, the present invention is directed to enhancing the accuracy with which tooth restorations are performed, including the manner by which a tooth is prepared and fit with a dental prosthetic, such as a crown. Further, the present invention is directed to reducing the skill-dependent tasks associated with tooth restoration, while at the same time, improving the precision with which these procedures are performed. By improving the accuracy of restoration procedures, any need to repeat these procedures for a given patient can be eliminated and patient comfort can be improved. In addition, by improving the precision with which a prosthetic is prepared for attachment to the prepared tooth of a patient, durability and longevity of the prosthetic are improved. That is, when the interior of a prosthetic is not precisely fit to the prepared tooth of a patient, as in a case where the coping is undersized relative to the prepared tooth, buckling of the coping can occur. As a result, the buckling of the coping can cause the porcelain exterior of the prosthetic to crack. Because exemplary embodiments of the present invention provide a precise and accurate fit, they avoid such buckling of the prosthetic's interior, and therefore, improve the longevity of the prosthetic.

Exemplary embodiments of the present invention are thus directed to methods and devices for improving the process of tooth restoration. Exemplary embodiments relate to an apparatus and a process for producing a dental prosthetic comprising the steps: providing a prosthetic model; providing a prosthetic blank having exterior dimensions matched to those of said prosthetic model; forming an interior of said prosthetic model as a template; and matching an interior of said prosthetic blank to said prosthetic model.

BRIEF DESCRIPTION OF THE DRAWINGS

Other objects and advantages of the present invention will become more apparent from the following detailed description of the preferred embodiments when read in conjunction with the accompanying drawings, wherein like elements have been designated by like numerals, and wherein.

DETAILED DESCRIPTION OF THE PREFERRED EMBODIMENTS

To illustrate a process for fitting a patient with a dental prosthetic, exemplary embodiments will be described in the context of a prosthetic dental crown. However, those skilled in the art will appreciate that exemplary embodiments of the present invention can be used to produce any type of finished dental prosthetic, including inlays, onlays and bridges. To illustrate significant features which can be realized in accordance with exemplary embodiments of the present invention, reference is made to FIG. 1 and the fitting of a patient with a dental crown.

Figure 1:
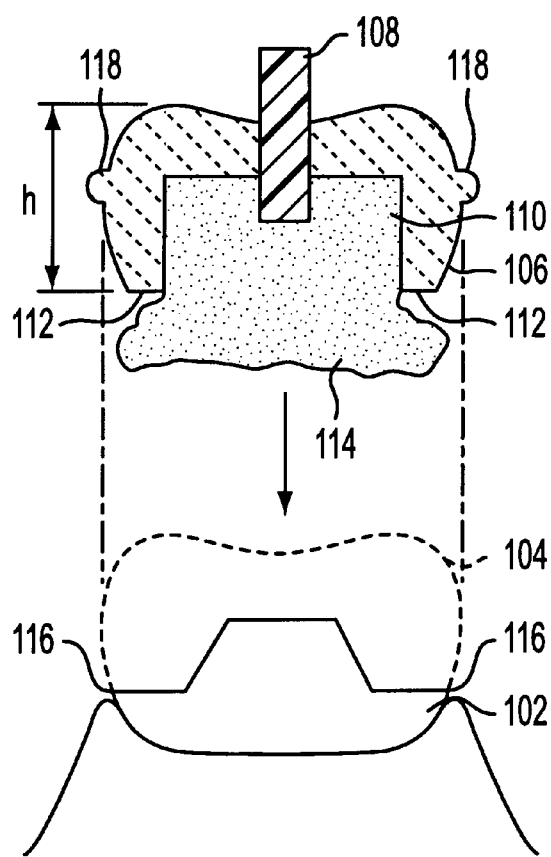
FIG. 1 illustrates a prosthetic model crown in accordance with an exemplary embodiment of the present invention.

In FIG. 1, a patient's tooth 102 is illustrated. To prepare the tooth for receiving a dental crown, the tooth is milled by the dentist in conventional manner. For example, the tooth is milled to remove the portion represented by dashed lines 104 using, for example, a diamond bur of a high speed hand tool.

In contrast to conventional techniques whereby an impression was necessarily taken of the prepared tooth for purposes of having a dental laboratory produce a coping which could be built-up using a finished crown material (such as porcelain), exemplary embodiments of the present invention avoid any need to take such an impression. Rather, in accordance with exemplary embodiments, a prosthetic model is provided. In the FIG. 1 embodiment, where a dental crown is to be prepared, the prosthetic model corresponds to a dental crown (i.e., a prosthetic model crown 106).

The prosthetic model crown 106 is selected from a series of such prosthetic models, which can be configured in a range of sizes, shapes, shades and types that cover the most common tooth sizes, shapes and shades. The prosthetic models can be substantially prefinished (e.g., seventy percent completed), and can be formed of any material, including any plastic, metal, or porcelain material. The range of sizes and types of prosthetic model crowns at the dentist's disposal correspond in size and type to a range of prosthetic blanks from which final dental prosthetics can be machined. In other words, the sizes and types of prosthetic model crowns correspond one-to-one with the range of sizes and types of prosthetic blanks used to provide finished dental crowns. As those skilled in the art will appreciate, the prosthetic model crowns can be formed of a first material (such as plastic), while the portion 114 prosthetic blanks from which the finished dental crowns are machined can be formed of a second, finished material (such as porcelain). Alternately, both the prosthetic model crowns and the prosthetic blanks can be formed of the same material. Any material which can be machined to an accuracy deemed satisfactory to the dentist can, of course, be used.

In accordance with an exemplary embodiment, the prosthetic model crown 106 is hollow, and can include a core plug 108. The core plug 108 can be inserted into a hole of the prosthetic model crown which extends from a biting surface of the prosthetic model crown to an interior thereof. The core plug 108 can be used to assist the dentist in removing the prosthetic model crown from the prepared tooth 102 of the patient after an accurate fit of the prosthetic model crown has been achieved.

Once the patient's tooth has been prepared to receive a dental prosthetic, and a prosthetic model crown 106 has been selected from the range of available sizes and types, the prosthetic model crown 106 is filled with a formable material that allows the dentist to achieve an accurate fit of the prosthetic model crown to the patient's prepared tooth and/or a duplicate model thereof. For example, the prosthetic model crown 106 can be filled with an ultraviolet light curing material 110, such as the material traditionally used for making dental impressions. As mentioned above, the prosthetic model crown can be produced with a hollow interior. Alternately, where the prosthetic model crown is provided to the dentist without a hollowed interior, the dentist can mill an interior of the prosthetic model crown to receive the ultraviolet light curing material. Those skilled in the art will appreciate that the accuracy of the milling is not critical, since the light cured material, once inserted into an interior of the prosthetic model crown, will fill in any gaps therein to ensure an accurate fitting to the prepared tooth. It is only necessary that an interior of the prosthetic model crown be hollowed to such a degree that allows the prosthetic model crown to completely fit over the prepared tooth.

Further, those skilled in the art will appreciate that a shoulder 112 of the prosthetic model crown can be initially provided, or can be milled, to a length shorter than the necessary height of the prosthetic blank. That is, the overall height "h" of the prosthetic model crown 116 can be intentionally configured shorter than the intended height of a prosthetic blank from which a finished dental crown will be machined. The use of a slightly shorter height for the prosthetic model crown will allow a gap to exist in a contact area between the bottom of the prosthetic model crown and the shoulder 116 of the tooth. As such, the dentist can apply light curing material to an interior of the prosthetic model crown and can allow a portion 114 of the light curing material 110 to protrude from an interior of the prosthetic model crown. The portion 114 of light curing material can be used to fill in the contact area between the shoulder 112 of the prosthetic model crown and the shoulder 116 of the prepared tooth so that an accurate template of the shoulder can be obtained with the light curing material.

Once the prosthetic model crown has been filled with the ultraviolet light curing material 110, the prosthetic model crown can be pressed over the prepared tooth, and aligned with adjacent teeth. When the dentist is satisfied with placement of the prosthetic model crown over the prepared tooth, the ultraviolet light curing material can be cured (i.e., exposed to ultraviolet light), and any excess material can be trimmed off (e.g., using a dental instrument). Further, exterior sides of the prosthetic model crown can be peripherally milled to adjust contact between the prosthetic model crown and adjacent teeth. As those skilled in the art will appreciate, because the shoulder 112 of the prosthetic model crown was formed to establish a gap in the contact area between the prosthetic model crown and the shoulder 116 of the prepared tooth, additional trimming of the light cured material in the shoulder contact area is unnecessary. Rather, placement of the prosthetic model crown to achieve accurate registration of occlusion (i.e., bite) is achieved prior to curing of the light cured material.

In addition to trimming excess light cured material and milling exterior sides of the prosthetic model crown to achieve appropriate contact with adjacent teeth, top surfaces of the prosthetic model crown can also be spot milled as necessary to achieve more exact occlusion. In alternate embodiments, the prosthetic model crown can, for example, be formed with a top surface material which is different in color than material used to form the remainder of the prosthetic model crown. Consequently, any spot milling or grinding of the top surface of the prosthetic model crown will be readily noticed, and can be accurately measured, to enhance the accuracy with which a final prosthetic blank is milled.

For example, a top surface of the prosthetic model can be formed with a uniform thickness (e.g., one millimeter) of material having a first color (e.g., red plastic). The remainder of the prosthetic model crown can, for example be formed of a clear plastic. Consequently, where any spot grinding of the top surface of the prosthetic model crown exceeds 1 millimeter in depth, this will be readily apparent because the red top surface will now be clear in that spot. As such, these spots can be given special attention during preparation of a final prosthetic dental crown which is produced using the prosthetic model crown.

Once the prosthetic model crown has been properly trimmed and milled to achieve an exact fit, it can be removed from the prepared tooth 102 for use as a template in milling a prosthetic blank to produce a final prosthetic dental crown. In accordance with exemplary embodiments, the final prosthetic dental crown is produced by milling a prosthetic blank which has exterior dimensions matched to those of the prosthetic model (i.e., prior to fitting of the prosthetic model crown to the prepared tooth in the manner described above).

To ensure that any modifications made to the prosthetic model crown can be made to the prosthetic blanks which is a substantially prefinished prosthetic crown, a proper registration of the orientation of the prosthetic model crown to the prosthetic blank is provided. More particularly, both the prosthetic model crown and the prosthetic blank are formed with registration features, such as registration marks 118 (e.g., protrusions of approximately 2 mm). The registration marks allow the prosthetic model crown which has been prepared in the manner described above to be placed in a holder with an orientation which matches an orientation of a prosthetic blank placed in a corresponding holder. The ability to hold the prosthetic model crown and the prosthetic blank at an exact, registered orientation allows the prosthetic blank to be milled to exactly match a shape of the prosthetic model crown which has been prepared.

The dentist can remove the prosthetic model crown from the prepared tooth by hand. Alternately, to simplify removal of the prosthetic crown from the prepared tooth once it has been trimmed and milled, the dentist can push inward on the core plug 108 (i.e., toward the prepared tooth), while pulling an exterior of the prosthetic model crown away from the prepared tooth. To further assist the dentist, a dental tool can be used to grab and hold exterior surfaces of the prosthetic model crown, while pushing inward on the core plug 108. Such a dental tool is illustrated in FIG. 2A.

Figures 2B, 2C:
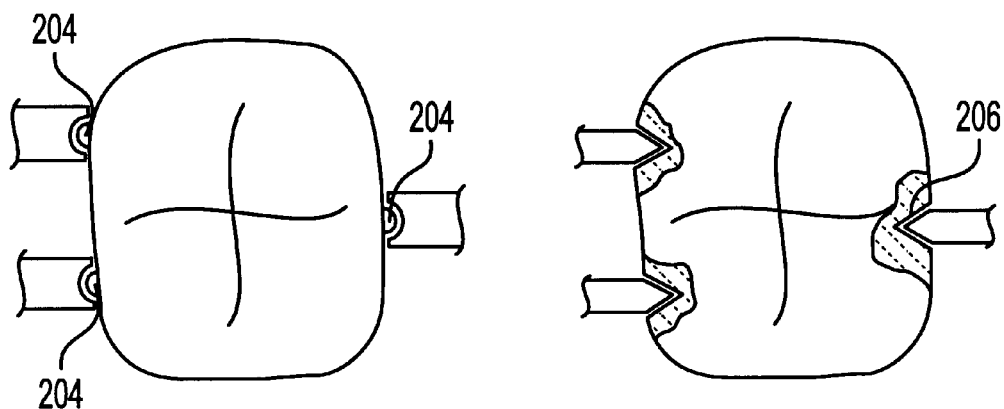
FIGS. 2A–2C illustrate exemplary embodiments of a method and apparatus for registering orientation, and for removing a prosthetic model or blank from a prepared tooth.
Figure 2A:
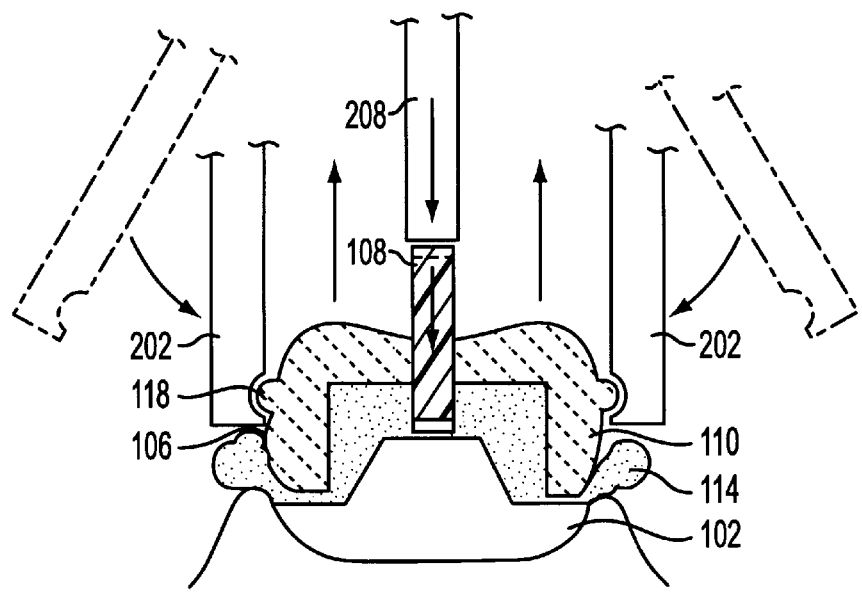

Referring to FIG. 2A, the dental tool includes clamps 202. In the exemplary FIG. 2A embodiment, the clamps 202 are configured to grab protruding, hemispherically-shaped elements 204 included on the prosthetic model crown. As those skilled in the art will appreciate, the hemispherically-shaped elements 204 (e.g., on the order of 0.5 to 2 mm or greater) can also serve as the registration marks 118 of FIG. 1. For example, as illustrated in FIG. 2B, the hemispherically-shaped elements 204 can be included at three locations on a periphery of the prosthetic model crown so that an exact orientation of the prosthetic model crown can be established.

As those skilled in the art will further appreciate, the elements 204 need not be hemispherically-shaped, but can be of any shape. Further, the elements 204 need not be formed as protrusions, but can be formed as recesses, such as the recesses 206 shown in FIG. 2C (e.g., recesses on the order of 0.5 to 2 mm or greater in depth). Of course, any modifications to the shape of the elements 204 can be accounted for in the shaped tips of the clamps 202 in the dental tool. Alternately, any form of registration mark, including optically detectable marks, can be used to provide the registration.

Referring again to FIG. 2A, the dental tool can be configured such that when pressure is applied inward on the pin 208 to push the core plug 108 against the prepared tooth 102, the clamps 202 are pressed inward against a periphery of the prosthetic model crown 106. For this purpose, at least one of the clamps is movable inward. The other clamps can be fixed, or can also be movable. Using such a tool, the dentist can easily remove the prosthetic model crown 106 from the prepared tooth 102.

Because an interior of the prosthetic model crown has been formed as a template representing a desired fit of the prosthetic model crown to the prepared tooth, an interior of the prosthetic blank is matched to the prosthetic model crown. An exemplary method and apparatus for matching an interior of the prosthetic blank to the prosthetic model crown is illustrated in FIG. 3.

Figure 3:
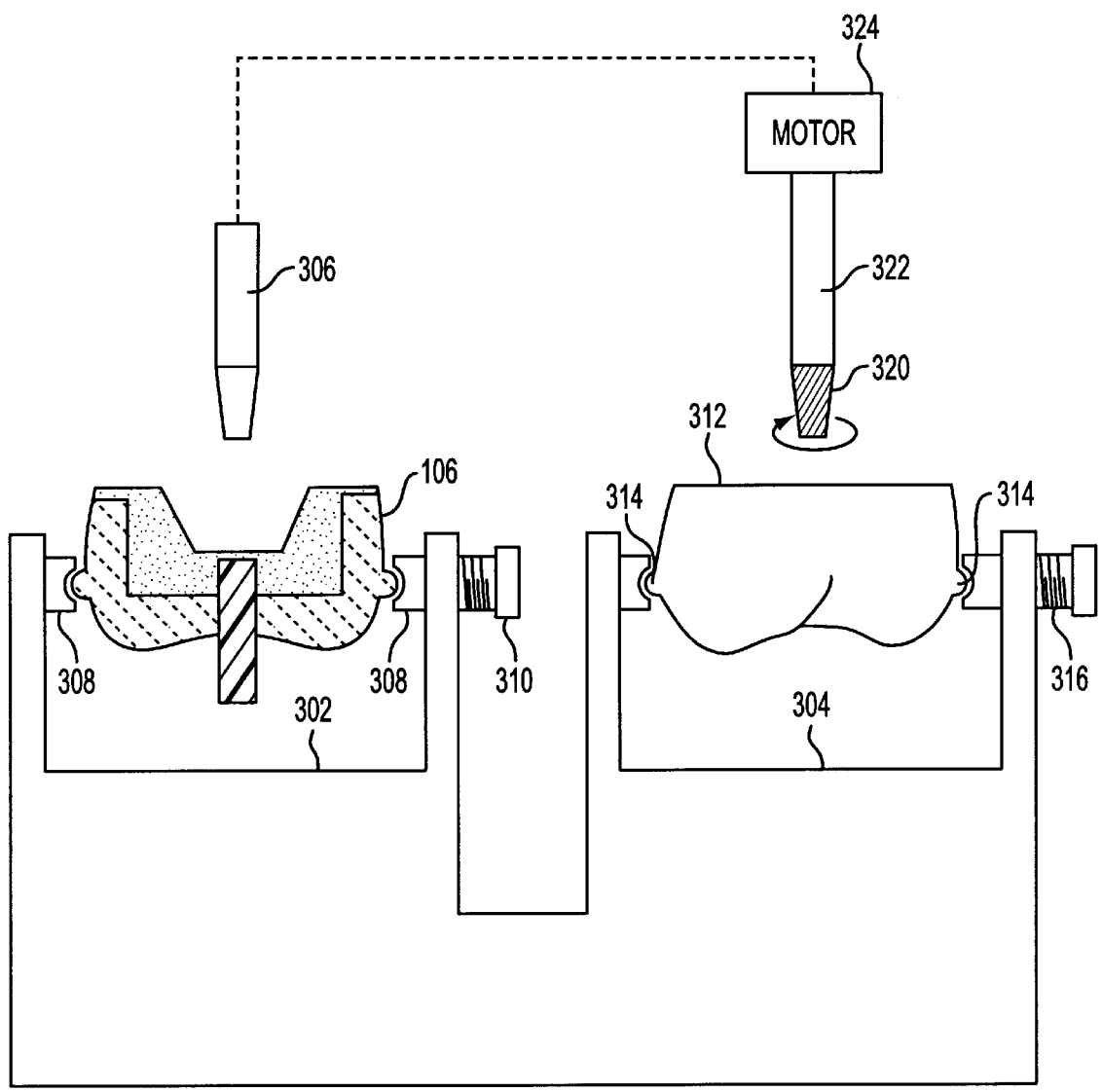
FIG. 3 illustrates an exemplary embodiment of a method and apparatus for matching a prosthetic blank to a prosthetic model.

Referring to FIG. 3, the prosthetic model crown is placed into a holding means having a first holding fixture 302 and a second holding fixture 304. The holding fixtures can be configured to allow placement of the prosthetic model crown and prosthetic blank in either an upright or an upside-down orientation. The prosthetic model crown can, for example, be initially placed upside down in the first holding fixture 302 so that the interior formed with the cured ultraviolet light curing material is readily accessible by a tracing stylus 306.

In accordance with exemplary embodiments, clamps 308 are provided in each of the first and second holding fixtures. Locations of the clamps are matched to the registration marks of the prosthetic model crown and the prosthetic blank, respectively. In an exemplary embodiment, adjustable means are provided to allow the prosthetic model crown to be inserted into the holding fixture, and then retained in place. More particularly, referring to the exemplary FIG. 3 embodiment, an adjusting screw 310 is provided to apply pressure to an exterior of the prosthetic model crown via the clamps 308, to thereby fix the prosthetic model crown in place.

In the exemplary FIG. 3 embodiment, the three registration marks are used to hold the prosthetic model crown in place. However, as those skilled in the art will appreciate, any number of registration marks can be included on the prosthetic model crown to hold it in place within the holding fixture.

In addition to placing the prosthetic model crown into the first holding fixture 302, a prosthetic blank 312 is placed in the second holding fixture 304. As was the case with the prosthetic model crown, the prosthetic blank can be held in place via clamps 314 and an adjusting screw 316.

The FIG. 3 apparatus further includes means for machining the prosthetic crown blank 312 to match an interior of the prosthetic model crown 106. For example, exemplary embodiments include a cutting tool 320 mounted to a motor driven shaft 322, which in turn is driven by motor 324. The cutting tool can, of course, be any milling device, such as diamond burs used as conventional dental tools.

In accordance with exemplary embodiments, the prosthetic crown 312 can include finished exterior surfaces, with the exception of the surface that is to mate with the prepared tooth. Due to the use of the registration marks and clamps being in identical positions in the prosthetic model crown and on the prosthetic blank, a tracing of the prosthetic model crown as a template can be used to match an interior of the prosthetic blank to the shape of the prepared tooth.

For this purpose, the stylus 306 can be traced over the prosthetic model crown, with motions of the stylus being used to control movement of the cutting tool over an interior surface of the prosthetic blank. Because the registration marks are used to locate the prosthetic model crown and the prosthetic blank in exactly the same orientation, exact alignment of outside contours between the prosthetic model crown and the prosthetic blank can be assured, such that exact machining of the prosthetic blank interior can be achieved. Such machining can be performed in known fashion, such as in the manner described in the aforementioned U.S. Pat. No. 5,135,393, the contents of which are hereby incorporated by reference in their entirety.

Once an interior of the prosthetic blank has been achieved, exterior surfaces of the prosthetic model crown can be traced and used to achieve similar milling of an exterior of the prosthetic blank crown. That is, both peripheral side surfaces and the top surface of the prosthetic crown can be spot milled, with particular attention being payed to any areas on the top surface where the 1 millimeter, differently colored portion of the prosthetic model crown has been removed.

After all machining of the prosthetic blank has been completed, both the prosthetic model crown and the prosthetic blank crown can be removed from the holding fixtures. Locating features included on the prosthetic blank can then be ground or polished off or, in the case where they are formed as recesses, can be filled. Because all exterior surfaces of the prosthetic blank will be formed as finished surfaces, the prosthetic blank now constitutes a finished crown which requires no porcelain build-up or sintering, but which can be immediately bonded into place over the prepared tooth of the patient.

Thus, unlike the '393 patent wherein a hand made template is produced from an impression, after which a coping is machined that must be ultimately built-up and sintered, exemplary embodiments constitute a one step process for producing a final dental prosthetic from a prosthetic blank. As such, exemplary embodiments constitute a simple, quick and cost effective manner of providing dental prosthetics which achieve an extremely precise fit to even a poorly prepared tooth.

Of course, exemplary embodiments are not limited to the preparation of a prosthetic dental crown. For example, exemplary embodiments can also be used to produce a dental bridge. In an exemplary embodiment, a process and apparatus as described above with respect to the preparation of a prosthetic dental crown can be used to produce an entire dental bridge. In one exemplary embodiment, multiple prosthetic model crowns associated with a bridge can be produced in the manner described above. The multiple prosthetic model crowns can then be connected to one another using a light cure material and/or a connecting rod (such as a light cure cement) to form a template for a bridge. Multiple prosthetic blanks can then be connected to one another in a similar fashion, and subsequently machined by tracing the multiple prosthetic model crowns which form a bridge template.

Where multiple prosthetic crowns are connected using a connecting rod, such as a metal (e.g., stainless steel) rod, each of the individual prosthetic crowns in the bridge remains separate. As such, some tolerance of the bridge to bending is accommodated, such that the individual prosthetic crowns will not break due to stress in contacting one another when force is applied to the bridge.

Figure 4A:
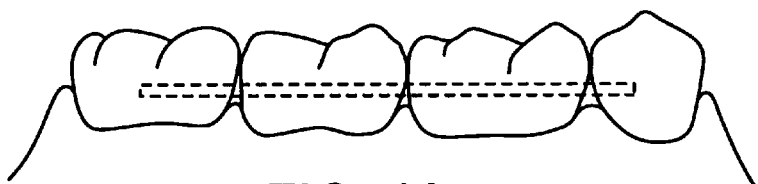
FIGS. 4A–4B illustrate use of exemplary embodiments of the present invention in the preparation of a prosthetic dental bridge.

In FIG. 4A, a bridge template is formed using multiple prosthetic model crowns which have been bound together using a light cure material and/or a connecting rod, such as a stainless steel rectangular rod supplied through a drilled channel within each of the prosthetic model crowns. The prosthetic dental bridge can be formed as multiple prosthetic dental crowns connected to one another in similar fashion.

Figure 4B:
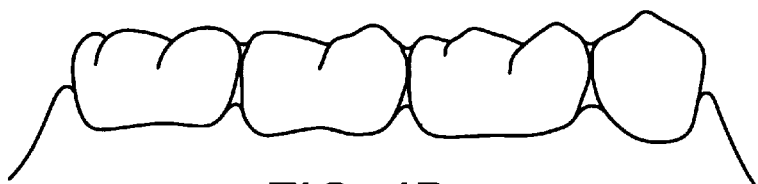

In an alternate embodiment, the multiple prosthetic model crowns used to form a bridge template can be traced in order to machine a single prosthetic blank formed large enough to serve as a bridge. FIG. 4B illustrates a prosthetic dental bridge formed as a unitary structure. In this case, the entire bridge is machined as a single piece from a template which can be formed in the manner as described with respect to FIG. 4A.

In another alternate embodiment, rather than using multiple prosthetic blanks to produce a bridge template, the bridge template can be formed as a pre-made unit. A blank prosthetic bridge can subsequently be machined, in a manner similar to that described above with respect to other embodiments of the present invention, by tracing the pre-made bridge unit representing a bridge template, to produce the finished bridge prosthetic.

Those skilled in the art will appreciate that exemplary embodiments of the present invention can also be used to machine prosthetic blanks into prosthetic inlays and onlays. That is, in accordance with exemplary embodiments of the present invention, an impression material can be placed into the inlay or onlay area of the patient's tooth, and a prefabricated prosthetic can be placed in the impression material. The impression material can then be cured and any excess impression material removed to provide a template of the inlay or onlay. Afterwards, a machining of a blank inlay or onlay can be performed using the prepared template in the manner described previously with respect to the prosthetic crown. As such, only the interior of a finished blank inlay or onlay is machined to match the blank to the template in a manner which will achieve an accurate and precise fit of the inlay or onlay.

Of course, those skilled in the art will appreciate that alternate embodiments of the present invention exist. For example, the FIG. 3 apparatus can be configured with adjustments to accommodate any size prosthetic model and/or prosthetic blank, or alternately, a separate apparatus can be configured for different types of teeth (e.g., one size for molars, one size for bicuspids and so forth).

Further, in accordance with exemplary embodiments, an interior of the prosthetic model crown and/or the prosthetic blank can be formed with a surface better suited to adhere with the prepared tooth. For example, the interior can be formed with annular serrations to improve the adherence of the prosthetic to the prepared tooth. Similarly, the prepared tooth can be formed with annular serrations about its exterior to enhance the adherence of the prosthetic thereto.

Previously, the use of such features to enhance the adhesion of the prosthetic to the prepared tooth could not be exploited, because it was necessary to repeatedly remove the prosthetic dental crown from the prepared tooth to repeatedly make adjustments before finally connecting it to the prepared tooth.

In accordance with alternate embodiments of the present invention, the prosthetic blanks can be produced to include a first exterior material (e.g., porcelain or ceramic), and a second interior material (e.g., metal, such as gold). As such, exemplary embodiments of the present invention can be used to produce a template for milling the second interior material of the prosthetic blank (e.g., mill a gold coping included within the blank). The use of the metal interior in the prosthetic blank allows the finished prosthetic to be cemented into place on the prepared tooth of a patient. As those skilled in the art will appreciate, cement, or other similar bonding agents, allow enhanced tolerance in attaching a prosthetic to a prepared tooth of a patient. This increased tolerance is relative to that associated with the typical bonding agents used with materials such as porcelain or ceramic. These materials require the use of bonding agents that tend to be more temperamental and labor intensive in their application.

In accordance with yet another embodiment, the prosthetic blank can be formed of a first material, such as porcelain or ceramic, and milled in accordance with exemplary embodiments of the present invention. Afterwards, the prepared interior of the prosthetic blank can be milled a predetermined amount (e.g., approximately 0.2 mm), to accommodate a coating of the interior with a second material more suitable for cementing the prosthetic to the prepared tooth of a patient. For example, a second material, such as metal (e.g., gold) can be applied to the milled interior of the prosthetic through, for example, electroplating.

Those skilled in the art will appreciate that where it is desirable to produce blanks formed of two materials, any techniques readily available can be used. For example, the prosthetic blanks can be produced by building up the first material (e.g., porcelain), on a standardized metal coping having a predetermined size and shape. The exposed side of the coping can then be machined using techniques described in accordance with exemplary embodiments of the present invention to fit the built-up coping to a patient's prepared tooth.

Figure 5A:
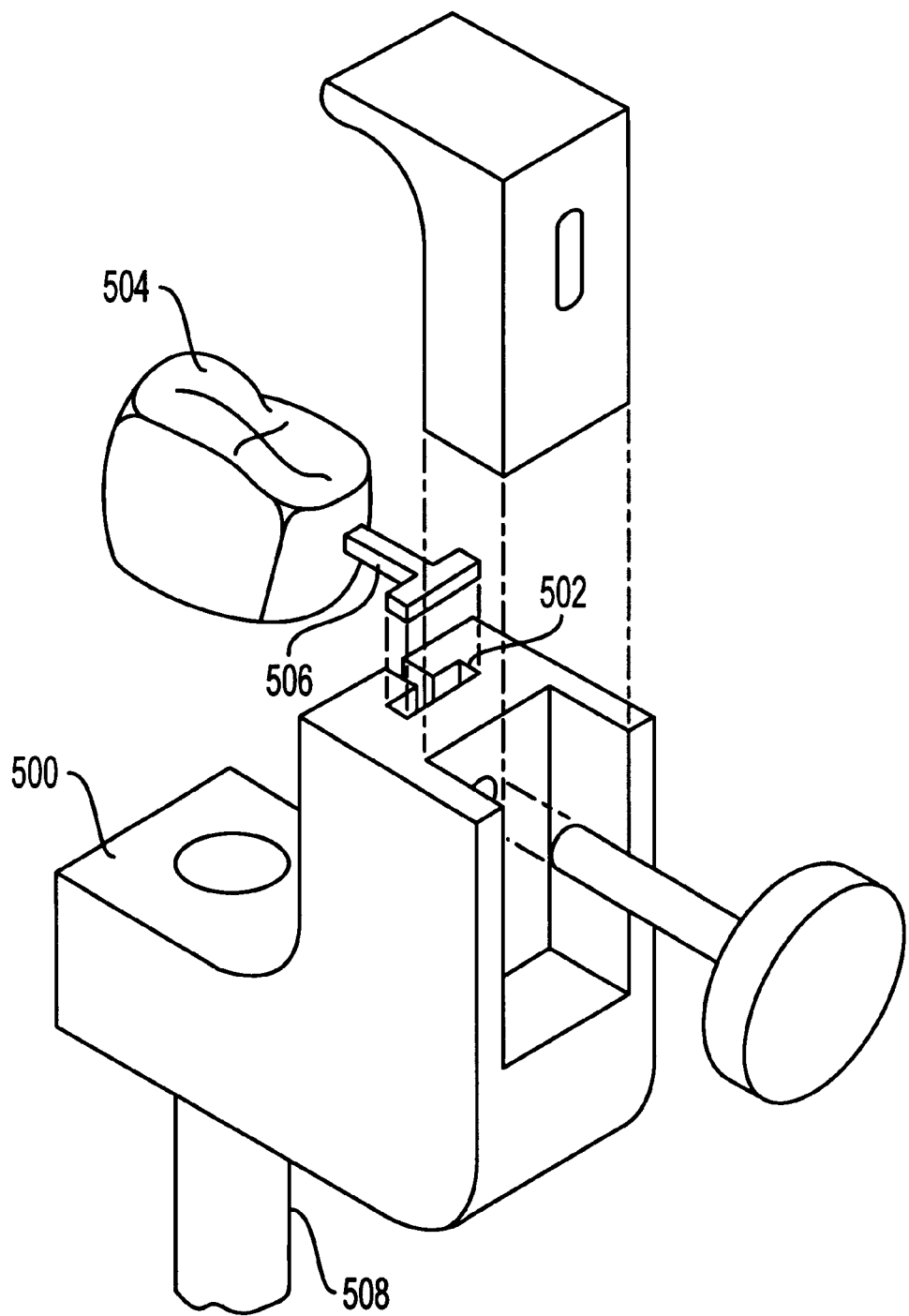
FIGS. 5A–5C illustrate an alternate exemplary embodiment of the present invention.
Figure 5B:
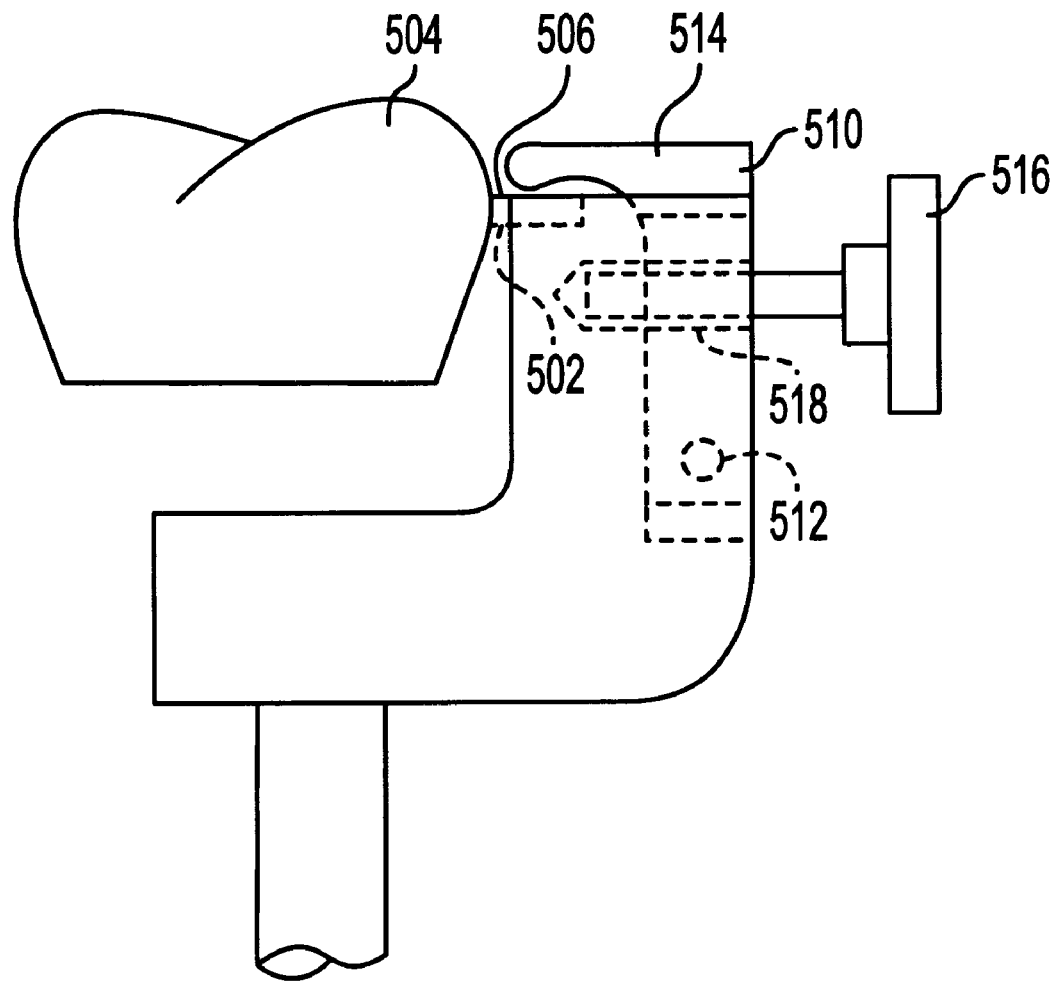
Figure 5C:
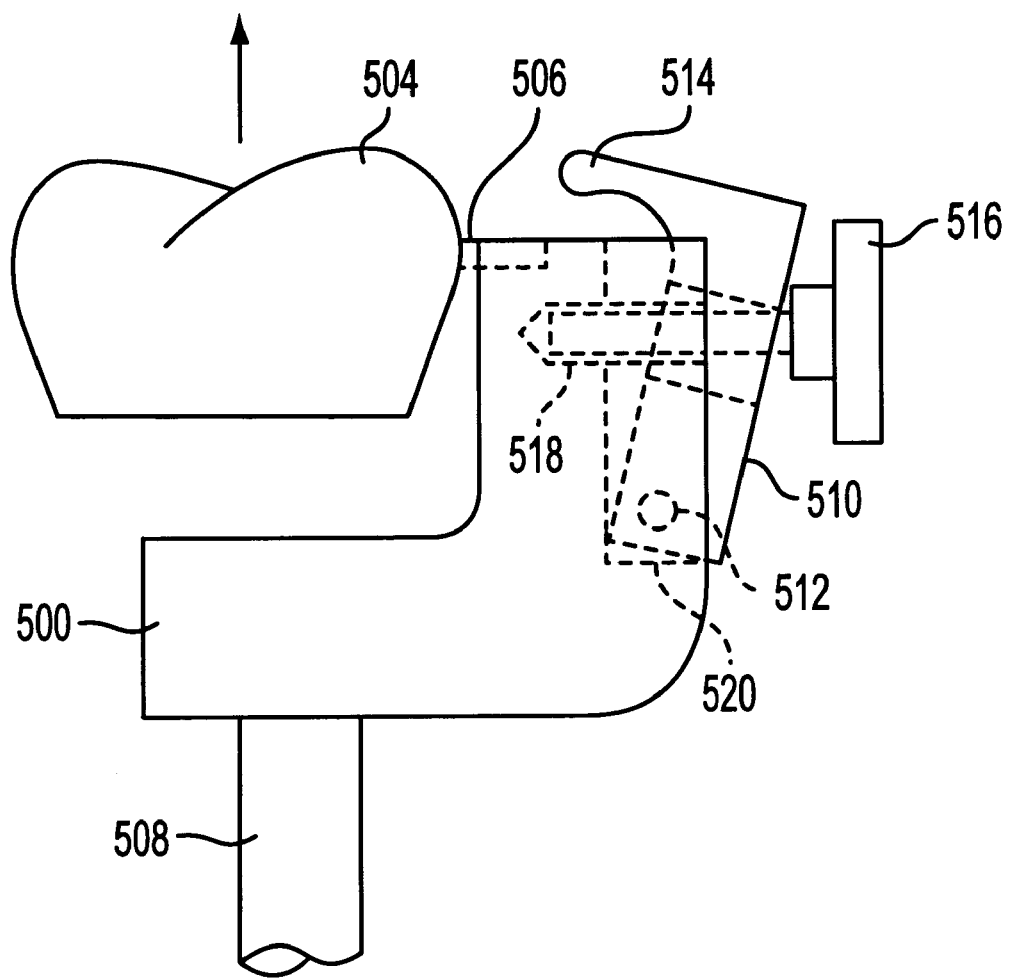

FIGS. 5A–5C illustrate an alternate exemplary embodiment of the present invention for configuring a prosthetic blank and/or prosthetic model crown, as well as a holding means which can be used in conjunction with a milling apparatus similar to that illustrated in FIG. 3. In FIG. 5A, a removable fixture 500 is provided, which can be mounted to the FIG. 3 apparatus, and which has a general "L" shape in the FIG. 5 embodiment. The fixture 500 includes a nested opening 502 which can be used to positively locate a prosthetic blank and/or a prosthetic model crown. The prosthetic blank and/or prosthetic model crown 504 can be configured, as illustrated in FIG. 5A. As illustrated therein, a registration mark is formed as a "T" shaped tang molded onto the periphery of the blank and/or crown as a male connector which can be mated to the nested opening 502 to positively register the blank/crown with the fixture 500. Of course, those skilled in the art will appreciate that the tang can be configured in any acceptable manner, provided a suitable mating can be achieved with respect to the fixture 500. The fixture 500 can be removably mounted into the FIG. 3 apparatus, via a rotatable shaft 508 which can be clamped into the FIG. 3 apparatus in a corresponding receptacle (not shown) included therein. Of course, similar fixtures 500 can be associated with either or both of the holding fixtures used in the FIG. 3 apparatus for the prosthetic blank and/or the prosthetic model crown.

FIG. 5B illustrates the mechanism which can be included with the locating fixture 500 to clamp the prosthetic blank or prosthetic model crown into the fixture. As illustrated in FIG. 5B, after the "T" shaped tang 506 has been inserted into the nested opening 502, a clamping mechanism 510, which is pivotable about a pivot 512, can be displaced such that a clamping tip 514 is located over the "T" shaped tang 506. A thumb screw 516 can then be used to lock the clamp 510 into place by, for example, rotating in a clockwise direction such that a screw 518 which passes through the clamp 510 can lock the clamp in a closed position.

FIG. 5C illustrates the clamp 510 in an open position. As illustrated in FIG. 5C, the thumb screw 516 has been rotated in a reverse, counterclockwise direction, thereby permitting the clamp 510 to be pivoted about axis 512 away from a position where the clamping tip 514 engages the "T" shaped tang 506. As such, the prosthetic blank and/or prosthetic model crown can be removed vertically from the fixture 500. As illustrated in FIG. 5C, the clamp 510 moves about the axis 512 within an opening 520 of the fixture 500.

In accordance with exemplary embodiments, the "T" shaped tang 506 can be formed of any suitable material. For example, the "T" shaped tang 506 can be configured of the same material used to produce the prosthetic blank and/or prosthetic model crown. After the prosthetic model crown has been prepared, it can be removed from the fixture 500 and then the "T" shaped tang can be removed therefrom (e.g., milled in the same way that the elements 204 of FIG. 2B are removed) and polished.

According to the present invention, once the prosthetic crown has been formed, and the tooth upon which the crown is to be placed has been prepared, the crown can be inserted into place. In accordance with exemplary embodiments, any technique used for cementing a crown into place can be used. For example, a light cured cement can be used whereby the crown is inserted into place and, after all adjustments have been made, is exposed to a relatively high intensity light to cure the cement. In addition, known techniques which improve seating of the crown can be used, including techniques whereby small holes are inserted into the top of the crown to allow cement to be released therefrom during placement of the crown on the prepared tooth.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An apparatus for producing a dental prosthetic comprising:

means for holding a dental prosthetic model and a dental prosthetic blank having exterior dimensions matched to those of said prosthetic model, said holding means being configured to receive and register said matched exterior dimensions of said dental prosthetic model with said matched exterior dimensions of said dental prosthetic blank; and means for machining a surface of said dental prosthetic blank to match a surface of said dental prosthetic model.

2. An apparatus according to claim 1, wherein said surface of said dental prosthetic model is an interior surface formed of a formable, curable material shaped to match a prepared tooth of a patient.

3. An apparatus according to claim 2, wherein said formable, curable material is a light cured material.

4. An apparatus according to claim 1, wherein said machining means removes any portions of external surfaces of said dental prosthetic model necessary to achieve at least one of desired contact of said dental prosthetic model with adjacent teeth of a patient and desired patient occlusion.

5. An apparatus according to claim 1, in further combination with a dental prosthetic model, said dental prosthetic model comprising:

registration marks on external surfaces.

6. An apparatus according to claim 5, in further combination with a dental prosthetic blank, said dental prosthetic blank further including:

registration marks on external surfaces, the registration marks of said dental prosthetic blank being matched in location to the registration marks of said dental prosthetic model.

7. An apparatus according to claim 6, wherein said dental prosthetic blank and said dental prosthetic model include registration marks formed as "T" shaped tangs, said apparatus further including:

fixtures having surfaces which mate to said "T" shaped tangs of said dental prosthetic blank and said dental prosthetic model.

8. An apparatus according to claim 5, wherein said registration marks are formed as a "T" shaped tang which mates to a fixture used to register a position of said prosthetic model in said apparatus.

9. A dental prosthetic blank comprising:

an external surface; and registration marks formed on said external surface, said registration marks being matched in location to registration marks of a dental prosthetic model.

10. A dental prosthetic blank according to claim 9, further comprising:

a predetermined size and shape matched to a size and shape of said dental prosthetic model.

11. A dental prosthetic blank according to claim 9, formed of a material used for a prosthetic dental crown.

12. A dental prosthetic blank according to claim 9, in combination with said dental prosthetic model, wherein said dental prosthetic model further includes:

a first surface formed with material of a first color; and a second portion formed with material of a second color.

* * * * *